United States Patent [19]

Abdulla et al.

[11] 4,288,624

[45] Sep. 8, 1981

[54] ACYLATION OR SULFENYLATION PROCESS

[75] Inventors: Riaz F. Abdulla, Greenfield; Lawrence A. Morgan, Indianapolis, both of Ind.

[73] Assignee: Eli Lilly and Company, Indianapolis, Ind.

[21] Appl. No.: 179,584

[22] Filed: Aug. 21, 1980

[51] Int. Cl.$^3$ .................. C07C 85/24; C07D 295/08; C07D 295/10

[52] U.S. Cl. .................. 564/345; 542/427; 542/438; 542/440; 542/455; 564/340; 564/342; 564/343

[58] Field of Search ............... 564/345, 340, 342, 343; 542/455, 438, 440, 427

[56] References Cited

U.S. PATENT DOCUMENTS

| | | | |
|---|---|---|---|
| 3,452,001 | 6/1969 | Alt et al. | 564/340 |
| 4,152,136 | 5/1979 | Taylor | 71/90 |
| 4,175,087 | 11/1979 | Abdulla et al. | 260/586 R |

OTHER PUBLICATIONS

House Modern Synthetic Reactions, W. A. Benjamin Inc., N. Y., N. Y., 1965, pp. 191–193.
Yoshimoto et al., Tet. Letters 1973 (#1), pp. 39–42.
Vinick et al., Tet. Letters 1978, pp. 315–318.
Bryson et al., Tet. Letters 1974 (#45), pp. 3963–3966.
Gammill et al., Synthesis 1976, pp. 401–403.
Gassman et al., J. Org. Chem. 42 (1977), pp. 3236–3239.
Zoretic et al., J. Org. Chem. 41 (1976), pp. 3587–3589.

*Primary Examiner*—Arthur P. Demers
*Attorney, Agent, or Firm*—Joseph A. Jones; Arthur R. Whale

[57] ABSTRACT

A process or acylating or sulfenylating 1-amino-2-phenyl-1-butene-3-ones to prepare the corresponding 4-acyl or 4-substituted-thio compounds provides intermediates useful for preparing herbicides.

21 Claims, No Drawings

ACYLATION OR SULFENYLATION PROCESS

BACKGROUND OF THE INVENTION

1. Field of the Invention

This invention belongs to the field of synthetic organic chemistry and provides a novel method of acylating or sulfenylating an enaminone.

2. State of the Art

Enaminones similar to the products of the process of this invention were used as intermediates by Taylor, U.S. Pat. No. 4,152,136. The same patent shows, at its column 19, a conventional enamine acylation process. It will be understood that the acylation of enamines is old in the organic chemical art and is distinct from the process of this invention, which accomplishes the acylation or sulfenylation of an enaminone.

Organic chemists have known that an enaminone can be alkylated on the carbon $\gamma$ to the carbonyl group. See, for example, Bryson and Gammill, *Tetrahedron Letters* 45, 3963-66 (1974). The process of this invention, however, is the first to enable chemists to acylate or sulfenylate an enaminone on the carbon $\alpha$ to the carbonyl group.

SUMMARY OF THE INVENTION

This invention provides a process for preparing a compound of the formula

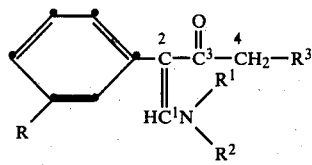

wherein R is chloro, bromo, fluoro or trifluoromethyl; $R^1$ and $R^2$ are independently $C_1-C_3$ alkyl, or $R^1$ and $R^2$ combine with the nitrogen atom to which they are attached to form pyrrolidino, piperidino, morpholino or N-methylpiperazino; $R^3$ is

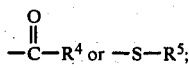

$R^4$ is $C_1-C_4$ alkyl, phenyl, $C_1-C_2$ alkyl monosubstituted with methoxy, or phenyl monosubstituted with chloro, bromo, fluoro or trifluoromethyl; $R^5$ is $C_1-C_3$ alkyl, $C_1-C_3$ fluoroalkyl, phenyl, benzyl, or phenyl substituted with $C_1-C_3$ alkyl, $C_1-C_3$ alkoxy or halo; which process comprises reacting an anion of the formula

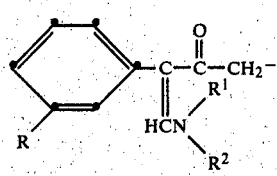

with a compound of the formula

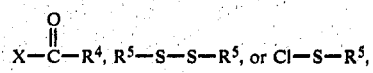

wherein X is chloro or bromo, in an inert organic solvent.

DESCRIPTION OF THE PREFERRED EMBODIMENTS

In this document, all temperatures will be expressed in degrees Celsius. All expressions of concentrations, percentages and the like will refer to weight measurements, unless otherwise stated.

In the above general formula, the general chemical terms $C_1-C_2$ alkyl, $C_1-C_3$ alkyl, $C_1-C_4$ alkyl, $C_1-C_3$ fluoroalkyl and $C_1-C_3$ alkoxy refer to groups such as methyl, ethyl, isopropyl, propyl, butyl, s-butyl, t-butyl, fluoromethyl, trifluoromethyl, 1,2-difluoromethyl, 3,3,3-trifluoropropyl, 3-fluorobutyl, 2-fluoropropyl, 2-fluoroisopropyl, methoxy and isopropoxy.

The use of the process of this invention to make certain classes of compounds is preferred. For example, the following limitations describe preferred classes of products, and also, necessarily, preferred classes of starting compounds. It will be understood that the limitations set out below may be combined to constitute further preferred classes:

a. R is trifluoromethyl;
b. R is chloro, bromo or fluoro;
c. $R^1$ and $R^2$ are methyl or ethyl;
d. $R^1$ and $R^2$ are methyl;
e. $R^4$ is $C_1-C_4$ alkyl or substituted $C_1-C_2$ alkyl;
f. $R^4$ is $C_1-C_4$ alkyl;
g. $R^4$ is t-butyl or methoxymethyl;
h. $R^5$ is $C_1-C_3$ alkyl;
i. $R^5$ is $C_1-C_3$ fluoroalkyl;
j. $R^5$ is phenyl or benzyl;
k. $R^5$ is phenyl substituted with alkyl, alkoxy or halo.

The compounds prepared by the process of this invention are intermediates useful for preparing herbicides. The use of the compounds will be discussed below.

The following compounds, which are produced by the use of the process of this invention, are mentioned to assure that the reader understands the invention.

2-(3-chlorophenyl)-1-ethylmethylamino-1-hexene-3,5-dione
2-(3-bromophenyl)-1-isopropylmethylamino-1-heptene-3,5-dione
2-(3-bromophenyl)-1-ethylpropylamino-1-nonene-3,5-dione
2-(3-fluorophenyl)-7-methyl-1-pyrrolidino-1-octene-3,5-dione
2-(3-fluorophenyl)-6-methyl-1-piperidino-1-heptene-3,5-dione
1-morpholino-5-phenyl-2-(3-trifluoromethyl-phenyl)-1-pentene-3,5-dione
2-(3-chlorophenyl)-7-methoxy-1-morpholino-1-heptene-3,5-dione
5-(3-chlorophenyl)-2-(3-fluorophenyl)-1-dipropylamino-1-pentene-3,5-dione
5-(4-bromophenyl)-1-pyrrolidino-2-(3-trifluoromethylphenyl)-1-pentene-3,5-dione
2-(3-bromophenyl)-1-ethylmethylamino-5-(2-fluorophenyl)-1-pentene-3,5-dione
2-(3-chlorophenyl)-1-methylpropylamino-5-(3-trifluoromethylphenyl)-1-pentene-3,5-dione
2-(3-chlorophenyl)-1-dimethylamino-4-methylthio-1-butene-3-one
2-(3-chlorophenyl)-1-dimethylamino-4-propylthio-1-butene-3-one 2-(3-bromophenyl)-1-diethylamino-4-isopropylthio-1-butene-3-one
4-(2-fluoroethylthio)-1-methylisopropylamino-2-(3-trifluoromethylphenyl)-1-butene-3-one
4-difluoromethylthio-2-(3-chlorophenyl)-1-piperidino-1-butene-3-one
2-(3-bromophenyl)-4-(3,3-difluoropropylthio)-1-pyrrolidino-1-butene-3-one
2-(3-bromophenyl)-4-pentafluoroethylthio-1-piperidino-1-butene-3-one
4-(2,2,3-trifluoropropylthio)-2-(3-fluorophenyl)-1-morpholino-1-butene-3-one
4-(2,3,3,3-tetrafluoropropylthio)-1-morpholino-2-(3-trifluoromethylphenyl)-1-butene-3-one
2-(3-chlorophenyl)-1-(N-methylpiperazino)-4-phenylthio-1-butene-3-one
4-benzylthio-2-(3-chlorophenyl)-1-(N-methylpiperazino)-1-butene-3-one
2-(3-bromophenyl)-1-dimethylamino-4-(2,4-dimethylphenylthio)-1-butene-3-one
1-diethylamino-2-(3-fluorophenyl)-4-benzylthio-1-butene-3-one
1-ethylisopropylamino-4-(2-ethylphenylthio)-2-(3-trifluoromethylphenyl)-1-butene-3-one
1-diethylamino-4-(3,5-dimethoxyphenylthio)-2-(3-trifluoromethylphenyl)-1-butene-3-one
2-(3-trifluoromethylphenyl)-4-(4-ethoxyphenylthio)-1-piperidino-1-butene-3-one
2-(3-bromophenyl)-4-(3-isopropoxyphenylthio)-1-pyrrolidino-1-butene-3-one
4-(2,6-dichlorophenylthio)-2-(3-fluorophenyl)-1-piperidino-1-butene-3-one
4-(3-bromophenylthio)-2-(3-bromophenyl)-1-piperidino-1-butene-3-one
2-(3-chlorophenyl)-4-(3,4-difluorophenylthio)-1-morpholino-1-butene-3-one
2-(3-chlorophenyl)-4-(3-iodophenylthio)-1-dimethylamino-1-butene-3-one
4-(3-chlorophenylthio)-2-(3-fluorophenyl)-1-(N-methylpiperazino)-1-butene-3-one The process of this invention is begun at low temperatures in the range of from about −60° to about −100°, preferably from about −70° to about −85°. It is preferred to allow the reaction mixture to warm to ambient temperature, about 15°–35°, after the reaction mixture is complete and the process has started.

The reaction of this process goes rapidly, and no unusual excess of reagents is necessary. In general, the stoichiometric amounts are adequate. As is usual in organic chemistry, it is economical to use a small excess, in the range of 1–20 percent, of less expensive reagents to assure that more expensive reagents are fully consumed.

The reaction is carried out in an inert organic solvent; the low temperature of the reaction and the reactivity of the reagents necessarily limit the solvents which may be used. The preferred inert organic solvents are ethers such as diethyl ether and, especially, tetrahydrofuran.

Hexamethylphosphoramide is preferably added to the reaction mixture as a co-solvent. The amount of hexamethylphosphoramide should be in the range of from about 10 percent to about 25 percent by volume of the reaction mixture.

The starting compounds for the process of this invention are the anions of enaminones as described above. The anions are formed by reacting the enaminones, all of which are known in the organic chemical art, with a strong base. As the examples below show, a highly preferred strong base is the amine anion formed by the reaction of butyllithium with diisopropylamine. Other related amine anions are also useful, such as those formed by the reaction of $C_1$–$C_4$ alkyllithium compounds with di($C_1$–$C_4$ alkyl)amines. For example, methyllithium, ethyllithium and isopropyllithium may be used with dimethylamine, diethylamine, ethylisopropylamine, di(s-butyl)amine, di(i-butyl)amine and the like. Other strong bases may be used as well, such as potassium hydride in the absence of secondary amine.

The starting anion is best prepared by first making a solution of the strong base in the solvent, and chilling the mixture to the desired operating temperature. The enaminone is then added, and the mixture is stirred at the low temperature for a time, from about a few minutes to about a few hours, to form the anion which is the starting compound for the process of this invention. The acylating agent or sulfenylating agent is then added, the reaction mixture is stirred at constant temperature for a time, and is then allowed to warm to ambient temperature. Total reaction times from about one hour to about twenty-four hours are adequate; longer reaction times up to even several days are not harmful to the process.

It is important to keep the reaction mixture substantially anhydrous. Thus, it is advisable to take care to use dry solvent, and to maintain an inert gas blanket over the reaction mixture to avoid the condensation of water from the air.

The products of this process are most easily isolated by washing the reaction mixture successively with aqueous acid and with aqueous base, and then chromatographing the washed organic solution over silica gel with eluting solvents composed of mixtures of esters and halogenated alkanes.

The following examples further illustrate the process of this invention. The products of the examples were identified by 60 megahertz nuclear magnetic resonance analysis, using tetramethylsilane as the internal standard.

EXAMPLE 1

6,6-Dimethyl-1-dimethylamino-2-(3-trifluoromethylphenyl)-1-heptene-3,5-dione

A 3.9 g. portion of diisopropylamine was dissolved in 200 ml. of dry tetrahydrofuran, and to the solution was added 16 ml. of 2.4-molar butyllithium solution in hexane. The mixture was stirred for 30 minutes and chilled to about −70°. To the mixture was added 10 g. of 1-dimethylamino-2-(3-trifluoromethylphenyl)-1-butene-3-one suspended in 50 ml. of tetrahydrofuran. The temperature rose to about −60°, and the mixture was stirred for 50 minutes and chilled. To the mixture was then added over a period of 1 minute a 4.7 g. portion of pivaloyl chloride. The temperature of the reaction mixture was then about −70°. The mixture was allowed to warm slowly to ambient temperature while it was stirred for 16 hours. The mixture was then diluted with 200 ml. of diethyl ether, and was washed successively with 1 N hydrochloric acid, 1 N sodium hydroxide, and saturated sodium chloride solution. The organic layer was then dried over magnesium sulfate, and was evaporated to dryness under vacuum to obtain 9.1 g. of a dark oil. The oil was chromatographed over a 300 g. silica gel column with 1:10 ethyl acetate:dichloromethane as the eluting solvent. The product-containing portions were combined and evaporated under vacuum to dryness to obtain 1.3 g. of the product, which was identified by nmr analysis, which showed (CDCl$_3$) δ1.03 (s, 9H); 2.78 (s, 6H); 5.03 (s, >1H); 7.53 (broad s, 4H); 7.76 (s, 1H).

EXAMPLE 2

1-Dimethylamino-6-methoxy-2-(3-trifluoromethylphenyl)-1-hexene-3,5-dione

A 3.9 g. portion of diisopropylamine was dissolved in 170 ml. of dry tetrahydrofuran, and the mixture was chilled under a nitrogen blanket to about −70°. Sixteen ml. of 2.4-molar n-butyllithium solution was added dropwise at constant temperature and the mixture was stirred for 55 minutes. To the mixture was then added 8.3 g. of 1-dimethylamino-2-(3-trifluoromethylphenyl)-1-butene-3-one dissolved in 25 ml. of tetrahydrofuran and 50 ml. of hexamethylphosphoramide over a period of 5 minutes. The mixture was stirred for 1 hour, and to it was added 4.2 g. of methoxyacetyl chloride dissolved in 40 ml. of tetrahydrofuran. The reaction mixture was then allowed to warm slowly to ambient temperature, and was stirred for 5 days. The mixture was then made acid to pH 5 with saturated potassium dihydrogen phosphate solution, and was partitioned between diethyl ether and water. The organic layer was washed with saturated sodium chloride solution, dried over magnesium sulfate and evaporated to dryness under vacuum. The residue was chromatographed on a 300 g. silica gel column with 15 percent ethyl acetate in dichloromethane as the eluting solvent. The product-containing fractions were combined and evaporated under vacuum to dryness to obtain 1 g. of the desired product, which was identified by conversion to the pyridinone in Preparation 2 below.

EXAMPLE 3

1-Dimethylamino-2-(3-trifluoromethylphenyl)-4-trifluoromethylthio-1-butene-3-one Two hundred ml. of dry tetrahydrofuran was combined with 8.1 g. of diisopropylamine, and the mixture was chilled to −70° under a nitrogen stream. A 36 ml. portion of 2.2-molar n-butyllithium in hexane was added, and the mixture was stirred for 5 minutes. Then a suspension of 18.8 g. of 1-dimethylamino-2-(3-trifluoromethylphenyl)-1-butene-3-one in 100 ml. of tetrahydrofuran was added at a rate such that the temperature of the mixture remained below −60°. The mixture was then stirred for 30 minutes more, and to it was added 10 g. of trifluoromethylsulfenyl chloride in 40 ml. of tetrahydrofuran, maintaining the temperature of the mixture below −60°. After the addition was complete, the reaction mixture was stirred for 15 minutes more, and was then allowed to warm to 10° over a period of 1 hour. The reaction was then quenched by the addition of saturated potassium dihydrogen phosphate solution and was diluted with water and diethyl ether. The organic layer was separated, dried over magnesium sulfate and evaporated to dryness under vacuum to obtain a dark oil which solidified on standing. The oil was chromatographed on a 500 g. silica gel column, with 1:9 ethyl acetate:dichloromethane as the eluting solvent. The product-containing fractions were combined and evaporated to dryness under vacuum to obtain 4.3 g. of the expected product, which was identified by nmr (CDCl$_3$): δ7.3–7.7 (m, 5H); 3.7 (s, 2H); 2.65 (s, 6H).

EXAMPLE 4

4-Benzylthio-1-dimethylamino-2-(3-trifluoromethylphenyl)-1-butene-3-one

A solution of 7.8 g. of diisopropylamine in 200 ml. of dry tetrahydrofuran was cooled under nitrogen. To the cold solution was added 32 ml. of 2.5-molar n-butyllithium solution in hexane, and the mixture was chilled to −70° and stirred for 30 minutes. To the mixture was added 10 g. of 1-dimethylamino-2-(3-trifluoromethylphenyl)-1-butene-3-one and 50 ml. of hexamethylphosphoramide in 25 ml. of tetrahydrofuran at a rate such that the temperature remained below −65°. The mixture was stirred for 30 minutes after the addition was complete, and then 9.7 g. of benzyl disulfide in 50 ml. of tetrahydrofuran was added while the reaction was held at constant temperature. When the addition was complete, the mixture was stirred for 15 minutes more at constant temperature, and was then allowed to warm to 8° with constant stirring over a period of about one hour. The reaction mixture was then diluted with 800 ml. diethyl ether and then washed successively with aqueous sodium hydroxide, hydrochloric acid and sodium chloride solution. The organic layer was then dried over magnesium sulfate, and was chromatographed on a silica gel column with 5% and then with 10% ethyl acetate in dichloromethane. The product-containing fractions were combined and evaporated to obtain 1.9 g. of the desired product which was identified by nmr (CDCl$_3$): δ7.75 (s, 1H); 7.3–7.6 (m, 9H aromatic); 3.9 (s, 2H); 3.15 (s, 2H); 2.8 (s, 6H).

The products of the process of this invention are used as intermediates for the preparation of 3-(acyl or substituted-thio)-1-alkyl-4(1H)-pyridinones, which are useful herbicides. The pyridinones are prepared by reacting a compound prepared above with either a formylating agent or an aminoformylating agent, which inserts a =CHOH or a =CHNR$^1$R$^2$ group, respectively, on the 4-position methylene group, and by exchanging with an amine of the formula R$^6$NH$_2$ to prepare a pyridinone of the formula:

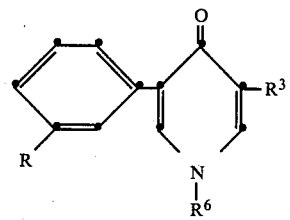

R$^6$ in the formula above is C$_1$–C$_3$ alkyl.

The formylation or aminoformylation, and the amine exchange, may be performed in either order. When the amine exchange is performed first, the =CHNR$^1$R$^2$ group of the pentenedione is converted to =CH$_2$NR$^6$. Insertion of the formyl or aminoformyl group then causes the compound to cyclize to form the desired pyridinone. If the formyl or aminoformyl group is inserted first, the amine exchange step causes immediate cyclization to form the pyridinone.

Alternatively, it is possible to prepare the 1-unsubstituted pyridinones by using NH$_3$ in place of R$^6$NH$_2$ in the process. The pyridinone is then alkylated at the 1-position with a halide of R$^6$, or with a dialkyl sulfate, according to common procedures.

As a chemist would expect, the amines, $R^6NH_2$, may be used in the form of salts, preferably hydrohalide salts, including hydrochlorides, hydrobromides and the like. Such salts are often more convenient than the free amines.

The formylating agents used in the process are chosen from the common agents used for such reactions. The preferred formylating agents are esters of formic acid of the formulae

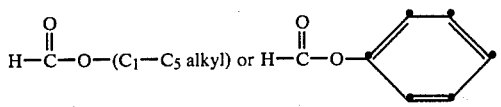

Similar formylations are discussed in Organic Syntheses 300-02 (Collective Vol. III 1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Diethyl ether is usually the preferred solvent. Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about −25° to about 10° is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a $=CHNR^1R^2$ group, or its acid addition salt. Such agents are chosen from among s-triazine, the orthoformamides, $HC[NR^1R^2]_3$ the formate ester aminals,

the formamide acetals,

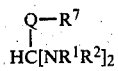

the tris(formylamino)methanes,

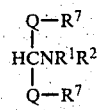

and preferably from the formiminium halides,

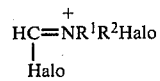

Q in the structures above represents oxygen or sulfur, and $R^7$ represents $C_1-C_6$ alkyl or phenyl.

Useful references on the aminoformylating agents include DeWolfe, Carboxylic Acid Derivatives 420-506 (Academic Press 1970), and Ulrich, Chemistry of Imidoyl Halides 87-96 (Plenum Press 1968). Bredereck et al. have written many papers on such agents and reactions, of which the following are typical. *Ber.* 101, 4048-56 (1968); *Ber.* 104, 2709-26 (1971); *Ber.* 106, 3732-42 (1973); *Ber.* 97, 3397-406 (1964); *Ann.* 762, 62-72 (1972); *Ber.* 97, 3407-17 (1964); *Ber.* 103, 210-21 (1970); *Angew. Chem.* 78, 147 (1966); *Ber.* 98, 2887-96 (1965); *Ber.* 96, 1505-14 (1963); *Ber.* 104, 3475-85 (1971); *Ber.* 101, 41-50 (1968); *Ber.* 106, 3725-31 (1973); and *Angew. Chem. Int'l. Ed.* 5, 132 (1966). Other notable papers on the subject include Kreutzberger et al., *Arch. der Pharm.* 301, 881-96 (1968); and 302, 362-75 (1969); Weingarten et al., *J. Org. Chem.* 32, 3293-94 (1967); and Abdulla and Brinkmeyer, *Tetrahedron* 35, 1675 (1979).

Aminoformylations are usually carried out without solvent, at elevated temperatures from about 50° to about 150°. Solvents such as dimethylformamide are sometimes used, however, particularly when it is desirable to raise the boiling point of the reaction mixture.

When aminoformylating with formiminium halides, however, aprotic solvents, such as described above in the description of solvents for formylation, are used at temperatures from about 0° to about 80°, preferably above room temperature. Halogenated solvents such as chloroform and methylene chloride can also be used in such aminoformylations if desired.

The exchange reactions with $R^6NH_2$ are best performed in protic solvents of which alkanols are preferred and ethanol is most appropriate. Temperatures from about −20° to about 100° can be used for the exchange reactions. Room temperature is satisfactory and is preferred.

The following preparations are offered to assure that agricultural chemists understand the preparation of the pyridinones.

PREPARATION 1

1-Methyl-3-(2,2-dimethylpropionyl)-5-(3-trifluoromethylphenyl)-4(1H)-pyridinone

A 3.6 g. portion of impure 6,6-dimethyl-1-dimethylamino-2-(3-trifluoromethylphenyl)-1-heptene-3,5-dione was dissolved in 17 ml. of N,N-dimethylformamide dimethyl acetal and stirred under reflux at about 100° overnight using a sub-surface nitrogen bubbler. The mixture was then evaporated under vacuum to obtain 3.5 g. of a dark oil, which was dissolved in 120 ml. of tetrahydrofuran and reacted with 15 ml. of 40% aqueous methylamine at ambient temperature for 1 hour. The mixture was then evaporated under vacuum, and the resulting oil was chromatographed on a 300 g. silica gel column with 2:3 ethyl acetate:dichloromethane as the eluting solvent. The product-containing fractions were combined and evaporated under vacuum, and the residue was triturated under hexane to obtain 0.6 g. of the desired product, m.p. 86°–88°, showing the following peaks on nmr analysis in DMSOd$_6$: δ7.6–8.2 (m, 6H, aromatic); 3.8 (s, 3H, N—CH$_3$); 1.2 (s, 9H, C(CH$_3$)$_3$).

PREPARATION 2

3-Methoxyacetyl-1-methyl-5-(3-trifluoromethylphenyl)-4(1H)-pyridinone

A 1 g. portion of impure 1-dimethylamino-6-methoxy-2-(3-trifluoromethylphenyl)-1-hexene-3,5-dione was reacted with 10 ml. of N,N-dimethylformamide dimethyl acetal, and then with 5 ml. of 40% aqueous methylamine, as described in Preparation 1. The product was purified as described in that example, except that 1:1 ethyl acetate:dichloromethane was used as the eluent, to obtain 0.13 g. of the desired product, m.p. 104°, dec. Nmr analysis in DMSOd$_6$ showed peaks at δ7.6–8.5 (m, 6H, aromatic); 4.8 (s, 2H, COCH$_2$); 3.9 (s, 3H, N—CH$_3$); 3.4 (s, 3H, OCH$_3$).

We claim:

1. A process for preparing a compound of the formula

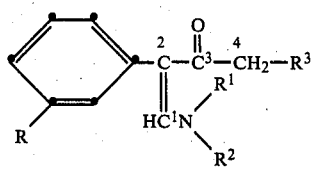

wherein R is chloro, bromo, fluoro or trifluoromethyl; R$^1$ and R$^2$ are independently C$_1$–C$_3$ alkyl, or R$^1$ and R$^2$ combine with the nitrogen atom to which they are attached to form pyrrolidino, piperidino, morpholino or N-methylpiperazino; R$^3$ is

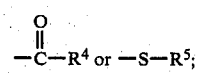

R$^4$ is C$_1$–C$_4$ alkyl, phenyl, C$_1$–C$_2$ alkyl monosubstituted with methoxy, or phenyl monosubstituted with chloro, bromo, fluoro or trifluoromethyl; R$^5$ is C$_1$–C$_3$ alkyl, C$_1$–C$_3$ fluoroalkyl, phenyl, benzyl, or phenyl substituted with C$_1$–C$_3$ alkyl, C$_1$–C$_3$ alkoxy or halo; which process comprises reacting an anion of the formula

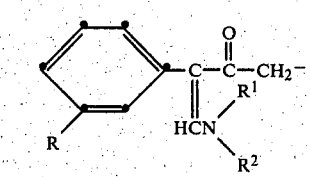

with a compound of the formula

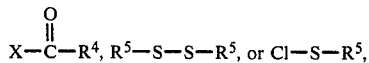

wherein X is chloro or bromo, in an inert organic solvent.

2. A process of claim 1 wherein the process is carried out at a temperature from about −60° to about −100°.

3. A process of claim 2 wherein the process is carried out at a temperature from about −70° to about −85°.

4. A process of claim 1 wherein the process is begun at a temperature from about −70° to about −85° and is raised to about the ambient temperature.

5. A process of claim 1 wherein the inert organic solvent is an ether.

6. A process of claim 2 wherein the inert organic solvent is an ether.

7. A process of claim 3 wherein the inert organic solvent is an ether.

8. A process of claim 4 wherein the inert organic solvent is an ether.

9. A process of claim 5, 6, 7 or 8 wherein the inert organic solvent is tetrahydrofuran and hexamethylphosphoramide is present as a co-solvent.

10. A process of claim 1 wherein the anion and the product are compounds wherein R is trifluoromethyl.

11. A process of claim 10 wherein the anion and the product are compounds wherein R$^1$ and R$^2$ are methyl or ethyl.

12. A process of claim 11 wherein the anion is reacted with a compound of the formula

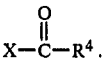

13. A process of claim 12 wherein R$^4$ is C$_1$–C$_4$ alkyl or C$_1$–C$_2$ alkyl monosubstituted with methoxy.

14. A process of claim 11 wherein the anion is reacted with a compound of the formula

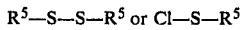

15. A process of claim 14 wherein R$^5$ is C$_1$–C$_3$ fluoroalkyl or benzyl.

16. A process of claim 13 wherein the anion of 1-dimethylamino-2-(3-trifluoromethylphenyl)-1-butene-3-one is reacted with pivaloyl chloride.

17. A process of claim 13 wherein the anion of 1-dimethylamino-2-(3-trifluoromethylphenyl)-1-butene-3-one is reacted with methoxyacetyl chloride.

18. A process of claim 15 wherein the anion of 1-dimethylamino-2-(3-trifluoromethylphenyl)-1-butene-3-one is reacted with trifluoromethylsulfenyl chloride.

19. A process of claim 15 wherein the anion of 1-dimethylamino-2-(3-trifluoromethylphenyl)-1-butene-3-one is reacted with benzyl disulfide.

20. A process of any one of claims 10–19 wherein the inert organic solvent is tetrahydrofuran, and hexamethylphosphoramide is present as a co-solvent.

21. A process of claim 20 wherein the process is begun at from about −70° to about −85° and is then raised to about the ambient temperature.

* * * * *